_United States Patent_ [19]

Laas et al.

[11] 4,301,084

[45] Nov. 17, 1981

[54] PROCESS FOR THE PREPARATION OF CARBOXYLIC ACID ESTERS OF β-FORMYL-CROTYL ALCOHOL BY AN ALLYL REARRANGEMENT

[75] Inventors: Harald Laas, Maxdorf; Axel Nissen, Leimen; Bernd Meissner, Heidelberg, all of Fed. Rep. of Germany

[73] Assignee: BASF Aktiengesellschaft, Fed. Rep. of Germany

[21] Appl. No.: 71,478

[22] Filed: Aug. 31, 1979

[51] Int. Cl.$^3$ .................. C07C 67/293; C07C 67/297; C07C 69/007; C07C 69/145
[52] U.S. Cl. ...................................... 260/405.6; 560/1; 560/8; 560/55; 560/64; 560/105; 560/112; 560/113; 560/125; 560/126; 560/187; 560/226; 560/230; 560/238; 560/240; 560/262; 560/265; 562/607; 568/876; 568/877; 568/878
[58] Field of Search ............... 560/125, 238, 262, 240, 560/112, 113, 1, 105, 230, 226, 8, 55, 64, 126, 187; 260/405.6

[56] References Cited

U.S. PATENT DOCUMENTS 3,639,437  2/1972  Fischer et al. ...................... 560/262

FOREIGN PATENT DOCUMENTS 1297597  6/1969  Fed. Rep. of Germany .

Primary Examiner—Vivian Garner
Attorney, Agent, or Firm—Keil & Witherspoon

[57] ABSTRACT

In a process for the preparation of a carboxylic acid ester of β-formyl-crotyl alcohol by rearrangement of the corresponding carboxylic acid ester of 2-formyl-2-hydroxy-but-3-ene or of an acetal or acylate thereof in the presence of copper or a copper compound, followed, where relevant, by hydrolytic cleavage of the acetal or acylate, more especially in the preparation of 4,4-dimethoxy-3-methyl-crotyl acetate, the yield is improved by carrying out the rearrangement in the presence of copper (I) chloride as the catalyst and ensuring that low-boiling by-products formed during the rearrangement are removed.

The products are of great importance as starting materials for an industrial synthesis of vitamin A and its derivatives.

3 Claims, No Drawings

PROCESS FOR THE PREPARATION OF CARBOXYLIC ACID ESTERS OF β-FORMYL-CROTYL ALCOHOL BY AN ALLYL REARRANGEMENT

The present invention relates to an improvement of a process for the preparation of a carboxylic acid ester of β-formyl-crotyl alcohol by rearrangement of the corresponding carboxylic acid ester of 2-formyl-2-hydroxy-but-3-ene or of an acetal or acylate thereof in the presence of copper or of a copper compound, followed, where relevant, by hydrolytic cleavage of the acetal or acylate, and more especially to an improvement in the preparation of 4,4-dimethoxy-3-methyl-crotyl acetate (3-dimethoxy-methyl-crotyl acetate) from 1,1-dimethoxy-2-methyl-2-acetoxy-but-1-ene.

It is known that the carboxylic acid esters of β-formyl-crotyl alcohol are of great industrial importance since they are used, inter alia, as starting materials for an industrial synthesis of vitamin A and its derivatives. Great effort has therefore gone into seeking an industrially advantageous process for their preparation. The best prior art process is probably that disclosed in German Pat. No. 1,297,597, according to which a carboxylic acid ester of β-formyl-crotyl alcohol is obtained by heating the corresponding carboxylic acid ester of 2-formyl-2-hydroxy-but-3-ene or an acetal or acylate thereof in the presence of copper or of a copper compound, followed, where relevant, by subsequent hydrolytic cleavage of the acetal or acylate. The allyl rearrangement in this process takes place with yields of up to 72.8%, whilst the subsequent hydrolytic cleavage is virtually quantitative.

The yields achieved by this process are insufficient to be satisfactory for industrial purposes and accordingly it is an object of the present invention further to improve the above process in respect of the achievable yields of β-formyl-crotyl acetate.

We have found, surprisingly, that this object is achieved and that a carboxylic acid ester of β-formyl-crotyl alcohol can be obtained, by the above allyl rearrangement in the presence of a copper compound, in yields of more than 80% and in very good space-time yields if the rearrangement is carried out in the presence of copper (I) chloride as the catalyst and care is taken that the low-boiling products formed as by-products by cleavage reactions during the rearrangement, for example, methanol, methyl acetate, acetic acid and water, are removed continuously from the reaction mixture.

Accordingly, the present invention relates to an improved process for the preparation of a carboxylic acid ester of β-formyl-crotyl alcohol by rearrangement of the corresponding carboxylic acid ester of 2-formyl-2-hydroxy-but-3-ene or of an acetal or acylate thereof in the presence of copper or a copper compound at from 50° to 250° C., preferably from 110° to 180° C., followed, where relevant, by hydrolytic cleavage of the acetal or acylate, wherein (a) the rearrangement is carried out in the presence of copper (I) chloride as the catalyst and (b) the low-boiling by-products formed during the rearrangement are removed in a conventional manner from the reaction mixture.

The removal of the low-boiling by-products formed during the rearrangement can be effected by distillation or, equally advantageously, by stripping by means of an inert gas flowing through the reaction mixture.

The starting materials can be prepared in the conventional manner by acylating 2-formyl-2-hydroxy-but-3-ene or an acetal or acylate thereof with an acid halide or acid anhydride of a suitable carboxylic acid. The starting materials can also be obtained by acylating 2-formyl-2-hydroxy-but-3-yne or an acetal or acylate thereof and subsequently partially hydrogenating the ester.

The ester groups in the starting materials can be derived, for example, from aliphatic, cycloaliphatic, araliphatic or aromatic carboxylic acids which in general are of 1 to 18 carbon atoms and may additionally carry inert substituents, for example, halogen. Preferred starting materials are those where the ester group is derived from a simple aliphatic carboxylic acid of 1 to 4 carbon atoms. Examples of carboxylic acids from which the ester group may be derived are cyclohexanecarboxylic acid, propionic acid, benzoic acid or palmitic acid, and especially acetic acid.

The starting material used may be a carboxylic acid ester of 2-formyl-2-hydroxy-but-3-ene as such or in the form of an acetal or acylate thereof, the acetals being preferred.

Amongst the acetals, those derived from simple aliphatic alcohols of 1 to 4 carbon atoms, e.g., methyl alcohol, ethyl alcohol or isopropyl alcohol, are preferred. Amongst the acylates, those derived from simple aliphatic carboxylic acids of 1 to 4 carbon atoms are preferred.

Examples of starting materials to be used in the process of the present invention are: 1,1-dimethoxy-, 1,1-diethoxy- and 1,1-di-n-butoxy-2-methyl-2-acetoxy-but-3-ene, 1,1-dimethoxy-2-methyl-2-benzoyloxy-but-3-ene, 2-(phenylacetoxy)-2-formyl-but-3-ene and 1,1-diacetoxy-2-methyl(chloroacetoxy)-but-3-ene. For practical reasons, 1,1-dimethoxy- and 1,1-diethoxy-2-methyl-2-acetoxy-but-3-ene are preferred.

Copper (I) chloride is used as the catalyst for the rearrangement, and may be employed unsupported or on an inert carrier. In general, the catalyst is used in an amount corresponding to from 0.005 to 5, advantageously from 0.05 to 0.5, percent by weight of copper, based on the starting material.

It was surprising that the use of copper (I) chloride, in conjunction with the removal of low-boiling products from the reaction mixture at the rate at which they are formed, should result in an increase in yield of about 10%. In contrast, when using other copper compounds, e.g., copper oxide, copper acetate, copper iodide, copper bromide or a mixture of copper compounds, removal of the low-boiling products from the reaction mixture during the rearrangement produces only insignificant improvements in yield (cf. the Comparative Examples).

The rearrangement is in general carried out at from 50° to 250° C., preferably from 110° to 180° C. At low temperatures, the reaction takes place very slowly. At temperatures above 180° C., there is a danger that decomposition products may form.

To carry out the process according to the invention, the starting compound is in general heated to the reaction temperature in a reaction vessel equipped with a stirrer, an internal thermometer and a descending condenser. The removal, in situ, of the low-boiling by-products formed during the rearrangement can be effected by continuously distilling these from the reaction mixture, either under atmospheric pressure or under reduced pressure, advantageously at from 100 to 500, preferably from 200 to 350, mbar.

Because of the large differences in boiling points, the removal of the low-boiling products is technically relatively simple. Both in the laboratory and on an industrial scale, it is merely necessary to ensure, by appropriate design of the condenser connected to the reaction vessel, that the low-boiling products can distil off whilst the amount of useful products removed remain below 0.5%.

Removal of the low-boiling products by stripping with an inert gas flowing through the reaction mixture is advantageously carried out with nitrogen or argon, but it is also possible to use such gases as $CO_2$, methane, hydrogen and methyl chloride.

In order to achieve an advantageous stripping effect, it is necessary to use about 20–300, preferably 100–200, liters of gas per kg of compound employed per hour.

If a carboxylic acid ester of 2-formyl-2-hydroxy-but-3-ene is used as the starting material, the rearrangement directly gives the carboxylic acid ester of $\beta$-formyl-crotyl alcohol. If, on the other hand, a corresponding acetal or acylate is used as the starting material, the rearrangement product obtained is the acetal or acylate of the carboxylic acid ester of $\beta$-formyl-crotyl alcohol, which is subsequently quantitatively converted to the end product by conventional hydrolysis. For this purpose, the rearranged acetal or acylate can be isolated and then hydrolyzed in a second operation. However, it can also be advantageous to convert the rearranged acetal or acylate to the end product in the same reaction vessel, without isolating the intermediate.

The rearrangement reaction in general requires from 2 to 10, preferably from 2 to 6 hours, depending on the temperature. The hydrolysis of the rearranged acetal or acylate in general requires from 0.5 to 2 hours, depending on the temperature and on the pH of the reaction mixture.

Using the process according to the invention, the carboxylic acid esters of $\beta$-formyl-crotyl alcohol, which are sought-after starting materials for an industrial synthesis of vitamin A and its derivatives, can be obtained in substantially better yields than by the conventional processes.

In the Examples which follow, parts are by weight.

The end point of the rearrangement reaction was in each case determined by examining small samples by gas chromatography.

EXAMPLE 1

(A) Reaction according to the invention 1,800 parts of 1,1-dimethoxy-2-methyl-2-acetoxy-but-3-ene and 1 part of copper (I) chloride were heated, with stirring, at 155°–160° C. in a reaction vessel equipped with a stirrer, an internal thermometer and a descending condenser, the degree of rearrangement being determined by examining small samples by gas chromatography. The low-boiling products formed distilled off continuously over the entire reaction time of 6 hours. Subsequent working up of the reaction mixture by distillation gave 1,444 parts of 4,4-dimethoxy-3-methyl-crotyl acetate. This corresponds to a yield of 80.2% of theory.

(B) Comparative Examples (a) Reaction in the presence of Cu (II) acetate, CuBr or CuI, under reflux 1,800 parts of 1,1-dimethoxy-2-methyl-2-acetoxy-but-3-ene and 3.6 parts of copper (II) acetate were heated, with stirring, at 165° C. in a reaction vessel equipped with a stirrer, an internal thermometer and a reflux condenser.

During the reaction time of 12 hours the reaction temperature slowly fell to 125° C. as a result of the low-boiling products, which were boiling under reflux. Subsequent working up of the reaction mixture by distillation gave 1,152 parts of 4,4-dimethoxy-3-methyl-crotyl acetate, corresponding to a yield of 64% of theory.

In a similar reaction with CuBr or CuI, the following results were achieved:

| Catalyst | Conversion [%] | Yield [%] |
|---|---|---|
| CuBr | 98.7 | 67.8 |
| CuI | 44.7 | 33.9 |

(b) Reaction in the presence of Cu (II) acetate, CuBr, CuI or CuO, with continuous distillation of the low-boiling products 1,800 parts of 1,1-dimethoxy-2-methyl-2-acetoxy-but-3-ene together with 3.6 parts of copper (II) acetate were heated, with stirring, for 12 hours at 152° C. in the reaction vessel described under (A). The low-boiling products formed distilled off continuously over the entire reaction period. Subsequent working up of the reaction mixture by distillation gave 1,278 parts of 4,4-dimethoxy-3-methyl-crotyl acetate, corresponding to a yield of 71% of theory.

In a similar reaction with CuBr, CuI or CuO, the following results were achieved:

| Catalyst | Conversion [%] | Yield [%] |
|---|---|---|
| CuBr | 97.8 | 73.1 |
| CuI | 46.9 | 36.2 |
| CuO | 98.6 | 74.1 |

EXAMPLE 2

(A) Reaction according to the invention 564 parts of 1,1-dimethoxy-2-methyl-2-acetoxy-but-3-ene and 0.3 parts of copper (I) chloride were heated, with stirring, at 147° C., under a pressure of 0.2 bar, in a reaction vessel equipped with a stirrer, an internal thermometer, and a descending condenser. During the reaction time of 7.5 hours, the low-boiling products formed distilled off continuously and the reaction temperature rose to 157° C. Subsequent working up of the reaction mixture by distillation gave 459 parts of 4,4-dimethoxy-3-methyl-crotyl acetate, corresponding to a yield of 81.4% of theory.

(B) Comparative Example

Reaction in the presence of copper (I) chloride without removal of the low-boiling products.

564 parts of 1,1-dimethoxy-2-methyl-2-acetoxy-but-3-ene and 0.3 part of copper (I) chloride were heated, with stirring, at 160° C. in a reaction vessel equipped with a stirrer, an internal thermometer and a reflux condenser. During the reaction time of 4 hours, the reaction temperature gradually fell to 146° C. as a result of the low-boiling products formed beginning to reflux. Subsequent working up of the reaction mixture by distillation gave 422 parts of 4,4-dimethoxy-3-methyl-crotyl acetate, corresponding to a yield of 74.8% of theory.

EXAMPLE 3

Rearrangement 564 g of 1,1-dimethoxy-2-methyl-2-acetoxy-but-3-ene and 0.3 g of copper (I) chloride were heated, with stirring, at 160° C. in a reaction vessel equipped with a stirrer, an internal thermometer and a descending condenser. Over the entire reaction time of 5 hours, a stream of nitrogen (90 liters/hour) was passed continuously through the reaction vessel. Subsequent working up of the reaction mixture by distillation gave 462 parts of 4,4-dimethoxy-3-methyl-crotyl acetate, corresponding to a yield of 81.9% of theory.

Hydrolysis

Per hour, 80 parts of 4,4-dimethoxy-3-methoxy-crotyl acetate and 70 parts of water were heated in a two-stage circulatory reactor to 80° C., with reflux cooling. The mean residence time was 30 minutes. After removing the water-methanol mixture by distillation, β-formyl-crotyl acetate was obtained in virtually quantitative yield.

We claim:

1. In a process for the preparation of a carboxylic acid ester of β-formyl-crotyl alcohol by rearrangement of the corresponding carboxylic acid ester of 2-formyl-2-hydroxy-but-3-ene or of an acetal or acylate thereof in the presence of copper or a copper compound at from 50° to 250° C. followed, where relevant, by hydrolytic cleavage of the acetal or acylate, the improvement wherein
   (a) the rearrangement is carried out in the presence of copper (I) chloride as the catalyst and
   (b) the low-boiling by-products formed during the rearrangement are continuously removed from the reaction mixture.

2. The process of claim 1, wherein low-boiling by-products formed during the rearrangement are continuously removed from the reaction mixture by distillation.

3. The process of claim 1, wherein low-boiling by-products formed during the rearrangement are continuously removed from the reaction mixture by stripping with an inert gas flowing through the reaction mixture.

* * * * *